United States Patent [19]

Malata et al.

[11] 4,114,276
[45] Sep. 19, 1978

[54] DENTAL TOOL HANDPIECE ASSEMBLY WITH REMOVABLE SPACER MEMBER

[75] Inventors: Peter Malata; Josef Buchsteiner, both of Bürmoos, Austria

[73] Assignee: Dentalwerk Bürmoos Gesellschaft m.b.H., Bürmoos, Austria

[21] Appl. No.: 794,332

[22] Filed: May 5, 1977

[30] Foreign Application Priority Data

May 6, 1976 [AT] Austria .................................. 3328/76

[51] Int. Cl.² .............................................. A61C 1/14
[52] U.S. Cl. ........................................ 32/26; 279/1 A; 408/226
[58] Field of Search ..................... 32/26, 27; 279/1 A; 408/226

[56] References Cited

U.S. PATENT DOCUMENTS

| | | | |
|---|---|---|---|
| 514,073 | 2/1894 | Hesse | 32/27 |
| 1,674,486 | 6/1928 | Stark | 32/26 |
| 1,765,362 | 6/1930 | Berry | 279/1 A |
| 3,923,413 | 12/1975 | Giles | 408/226 |

FOREIGN PATENT DOCUMENTS

| | | | |
|---|---|---|---|
| 1,121,544 | 8/1956 | France | 408/226 |
| 659,438 | 4/1938 | Fed. Rep. of Germany | 32/26 |
| 366,102 | 12/1922 | Fed. Rep. of Germany | 32/48 |

Primary Examiner—Louis G. Mancene
Assistant Examiner—John J. Wilson
Attorney, Agent, or Firm—Toren, McGeady and Stanger

[57] ABSTRACT

A dental tool handpiece is provided with a spacer member which may be inserted into the collet of the handpiece which normally receives the tool and which has longitudinal slots adapting the collet to grip the tool when in operative engagement therein. The spacer member adapts the handpiece assembly to receive a shorter tool member within the bore defined within the collet, and when a tool member whose length is too short to reach the normal abutment surface must be operatively engaged within the collet, the spacer member may be inserted therein to shorten the depth of the bore and provide a substitute abutment surface for the shorter tool member. The spacer member includes a handle portion which is located to extend to within one of the longitudinal slots of the collet in order to facilitate guiding of the spacer member in place within the collet.

8 Claims, 8 Drawing Figures

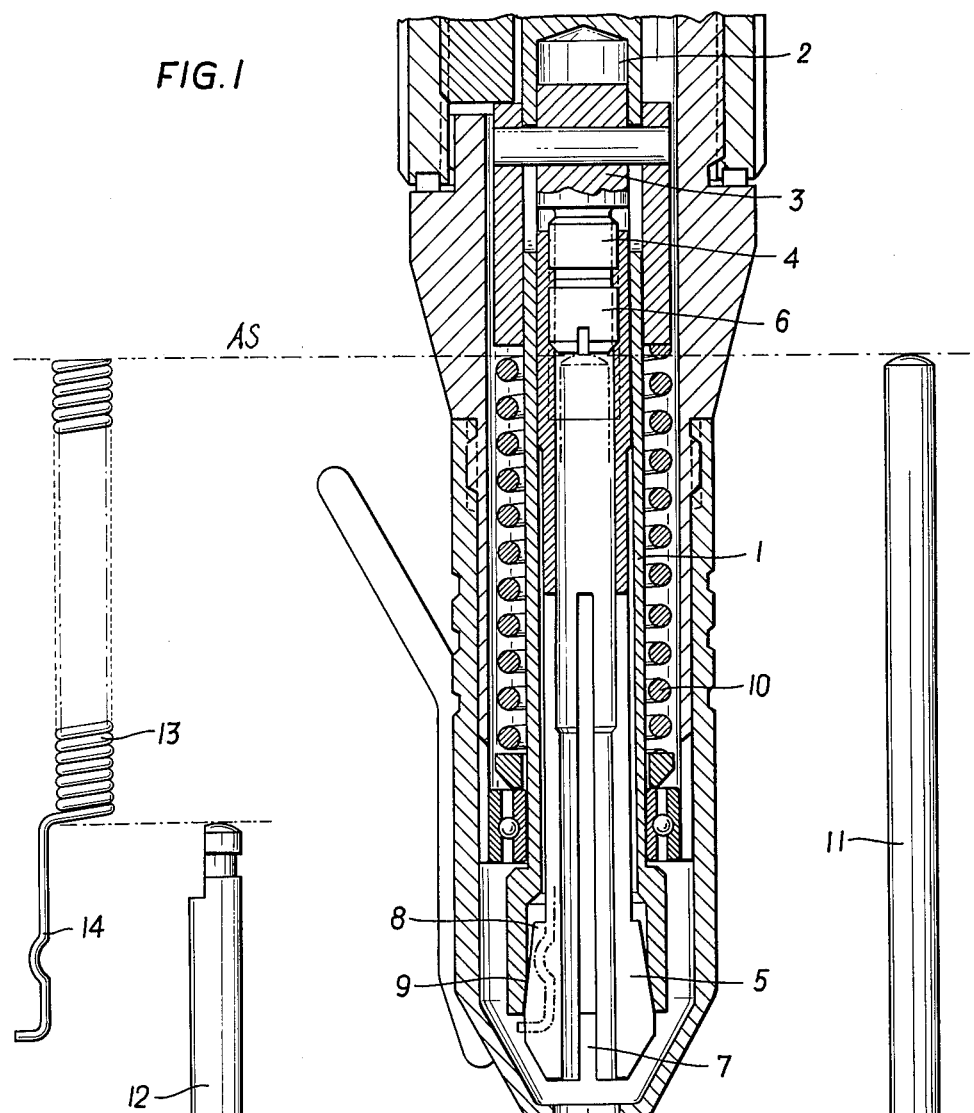
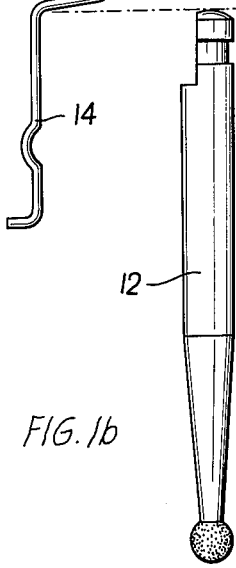
FIG. 1
FIG. 1b
Fig. 1a

DENTAL TOOL HANDPIECE ASSEMBLY WITH REMOVABLE SPACER MEMBER

BACKGROUND OF THE INVENTION

The present invention relates generally to tools used in the practice of dentistry and more particularly to the assembly of a dental tool handpiece wherein tool members are replaceably engaged during performance of dental operations.

In dental tool handpiece assemblies presently known in the art, the length of the shank or body portion of a tool, such as a drill or other device, which is normally inserted into the handpiece tends to be of a standardized size. In tools which utilize angled handpieces, the shank of a drill or similar tool member which is to be utilized with such a handpiece is usually much shorter than other shank lengths. However, there arises a need to enable tool members or drills of both types or categories to be inserted within a straight handpiece. In this connection, it is desirable also that drills with short shanks be provided with an axial abutment surface to support the drill in the same manner as would ordinarily occur with drills having longer shanks.

In order to achieve the purposes discussed above, pins have heretofore been utilized with dental tool handpieces. The pins are inserted into the bore defined by the collet of the handpiece and the length of the pin corresponds to the difference in the shank length of the tool members which are to be utilized thereby operating as spacer members to take up the gap between the shank end of the tool and the abutment surface provided within the handpiece.

However, pins of this type can be utilized satisfactorily only so long as they can be readily removed from the bore of the collet without difficulty when a tool member or drill is to be changed. Normally, it is necessary that such pins merely drop or fall out of the collet bore when the handpiece is held in a downwardly facing or oblique position. With increasing length of use of such pins within the collet, the collet tends to accumulate foreign matter or becomes disposed so that the pin will tend to stick within the collet making removal of the pin difficult or impossible. In such a case, the handpiece assembly must be disassembled and taken apart in order to enable removal of the pin. Generally, it is usually at least necessary that the collet be removed so that it may be reinserted in a manner providing an adjustment to insure the proper damping effects.

Operation of a dental handpiece without an abutment pin generally gives rise to the danger that the tool may slip into the collet and remain trapped there so that, again, the collet must be temporarily removed from the handpiece.

The present invention is directed toward providing a dental tool handpiece assembly which will facilitate utilization of tool members of different lengths and which will provide a substitute tool abutment surface within the bore of a handpiece tool collet when a shorter tool member must be used.

SUMMARY OF THE INVENTION

Briefly, the present invention may be described as a dental tool handpiece assembly comprising a collet which defines a bore into which a tool member is inserted for operative engagement within the handpiece. The collet is formed with longitudinal slots adapting the collet to grip the tool member for operative engagement within the handpiece assembly. The bore is defined with a predetermined depth terminating interioraly of the assembly at a tool abutment surface located to be engaged by the inner end of a tool member which is inserted into the bore. A removable spacer member may also be inserted into the bore to provide a substitute tool abutment surface thereby to adapt the handpiece assembly to receive therein a tool member which has a length which is too short to reach the tool abutment surface when the tool is placed is operative engagement within the bore. The removable spacer member is configured to include a handle which is located to extend to within one of the longitudinal slots in the collet when the spacer member is in place within the collet bore.

Thus, when a shortened tool member, such as a drill or the like, is to be utilized with the handpiece assembly of the present invention, the spacer member may be inserted into the handpiece assembly bore in order to shorten the length of the bore while still providing an abutment surface for the tool which is to be utilized. The spacer member is formed in such a way as to be easily inserted into the collet and the handle enables it also to be safely and conveniently removed therefrom. Thus, with the utilization of the spacer member of the invention, the handpiece may be adapted to provide a new tool member or drill abutment, so that further operations may be carried out therewith.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DESCRIPTION OF THE DRAWINGS

In the Drawings:

FIG. 1 is a sectional view of a handpiece assembly adapted to utilize the present invention;

FIG. 1a is a side view of a tool member such as a drill which may be utilized with the handpiece assembly of FIG. 1 without utilization of a spacer member;

FIG. 1b is a side view showing a spacer member and shortened tool member such as a drill which may be utilized with the handpiece assembly of FIG. 1;

DETAILED DESCRIPTION OF THE PREFERRED EMBODIMENTS

Figure 2:
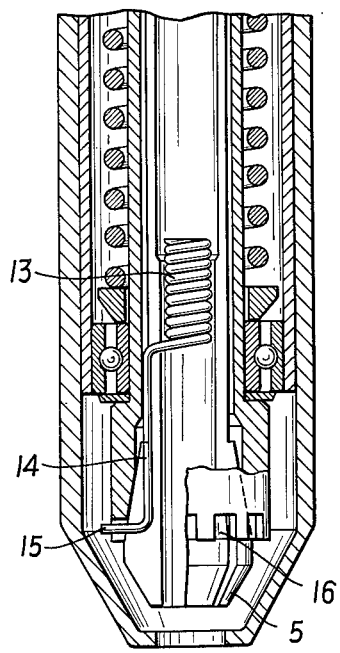
FIG. 2 is a sectional view showing a handpiece assembly with the spacer member of the present invention in place therein.

Referring now to the drawings, wherein similar parts are referred to with like reference numerals, and more particularly to FIGS. 1, 1a and 1b, there is shown in FIG. 1 a conventional dental tool handpiece assembly forming a part of the overall assembly of the present invention and which may be adapted in accordance with the present invention to receive a shortened tool member such as a drill or the like. The assembly shown in FIG. 1 includes a shaft member 1 provided with a longitudinal bore 2 within which a draw member 3 is mounted for lengthwise displacement against the force of a spring. The draw member 3 includes a threaded shoulder 4 onto which a collet 5 is screwed or threadedly secured by means of a lock screw 6.

The collet 5 is formed with several chuck slots 7 which extend longitudinally of the collet and with an outer cone member 8 which cooperates with an inner cone member 9 of an enlarged bore portion of the shaft 1.

The collet 5 may be shifted forwardly by displacing the draw member 3 in a forward direction so that the bore defined by the collet may be expanded to receive therein a tool member to be utilized with the handpiece of the invention. After insertion within the collet 5 of a tool member, a spring 10 will operate to bias the draw member 3 in the reverse direction and, as a result of the action of the spring 10, the collet 5 will be moved rearwardly of the tool so that its forward end will produce a clamping effect upon the shank of a tool inserted within the bore of the collet. The clamping action of the collet occurs as a result of the interaction of the outer and inner cone members 8, 9 sliding upon each other.

The tool member which is used with the handpiece assembly of FIG. 1 may comprise a drill 11 shown in FIG. 1a. The drill 11 is provided with a relatively long shank and when it is inserted into the collet 5 within the bore defined therethrough, the inner end of the drill 11 will become engaged against an abutment surface defined by the front face of the lock screw 6 and located along the dot-dash line AS.

However, if it is desired to use a shorter tool other than the drill 11, a problem may arise inasmuch as the tool may not be long enough to extend inwardly of the handpiece to abut against the abutment surface defined by the lock screw 6 along the line AS. An example of such a tool is a short handpiece drill 12 shown in FIG. 1b. When using a tool member such as the drill 12, it is advantageous to provide a bridging or spacer member which will occupy the distance between the inner end of the tool member and the abutment surface defined by the lock screw 6. Such a spacer member may be introduced into the bore of the collet before insertion of the tool and the tool may then abut against the outer end of the spacer member.

In accordance with the present invention, there may be provided for utilization with a short tool member such as the drill 12 a spacer member 13 which consists of a helically wound wire, one end of which is brought forwardly or outwardly of the handpiece assembly and then bent at an angle outwardly of the handpiece assembly thus forming a spacer member handle 14 which permits removal of the spacer member from the chuck of the handpiece assembly at any time. With the spacer member 13 inserted into the bore of the collet 5, the outer tip or bent end of the handle 14 will extend into one of the slots 7 of the collet and thereby not only facilitate insertion and alignment of the spacer member 13 within the collet bore but it will also facilitate removal of the spacer member when it is to be replaced.

Additionally, a spacer member constructed in accordance with the present invention may also be utilized for adjusting the collet. In such a case, the angularly bent end 15 of the handle, as best seen in FIG. 2, may be utilized to rotate the collet 5 thus facilitating the action of threadedly engaging the collet onto the lock screw 6 of the draw member 3.

After the desired position of the collet has been reached, the position of the collet may be secured by inserting the end 15 of the handle 14 into one of the front grooves 16 of the shaft one thus holding the collet against movement or rotation. As a result of this cooperation of elements, a lock screw then becomes superfluous.

Figure 3:
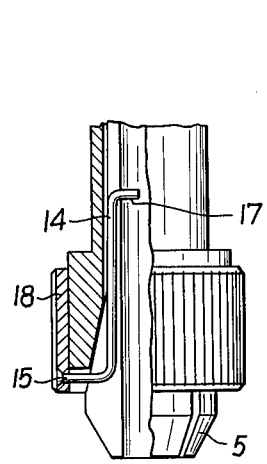
FIGS. 3, 4, 5 and 6 are partial sectional views showing other embodiments of the present invention.

Manipulation and operation of the spacer member 13 by handling the angularly bent end 15 of the handle 14 may be facilitated by an adjustment ring 18 within which the end 15 may be engaged with the ring 18 being pushed onto the front end of the shaft 1. As shown in FIG. 3, a configuration of an embodiment of the invention is shown with an end 17 which is bent radially inwardly of the handpiece assembly and which may form an inner abutment surface for tool members or drills having shorter shanks.

Figure 4:
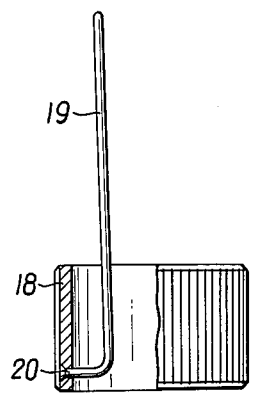

In order to assure fixation of the position of the collet when using drills with longer shanks, the ring 18 shown in FIG. 3 may be replaced by a ring 18 shown in FIG. 4. The ring shown in FIG. 4 carries a wire 19 having a free end which is outwardly elastic. It bears against the inner wall of the shaft 1 thus securing the ring 18 against axial displacement. A crooked portion 20 engages both in one of the front slots 16 and in one of the chuck slots 17 and thus impedes rotation of the collet relative to the hollow shaft 1.

Figure 5:
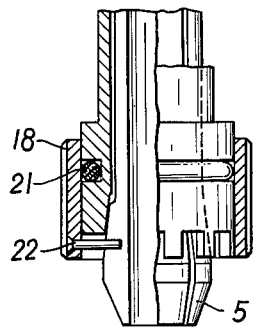
Figure 6:
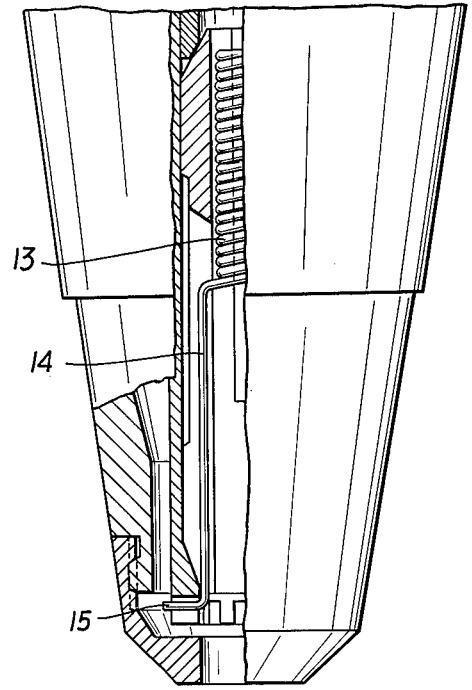

The invention is also applicable with an inner chuck cone, as shown in FIG. 5.

The fixation of the axial position of the applied ring 18 can be brought about also by an O-ring 21, as illustrated in FIG. 5. In this embodiment, a wire pin 22 assures that the position of the collet 5 will be maintained after it has been snapped into one of the front grooves 16 and the chuck grooves 7.

If the collet has oppositely directed chuck slots, the drill abutment may consist of a wire bent in a U formation with outwardly bent ends, this being a particularly simple approach.

Of course, it must be appreciated that the spacer member which provides the abutment surface need not be made of wire. The essential feature is that the introduced spacer member is provided with an extension such as a handle which will extend to the front end of the collet of the handpiece and which may be engaged within a chuck slot so that the handle member of the spacer member may be gripped for manipulation as previously described.

While specific embodiments of the invention have been shown and described in detail to illustrate the application of the inventive principles, it will be understood that the invention may be embodied otherwise without departing from such principles.

What is claimed is:

1. A dental tool handpiece assembly comprising a collet defining a bore into which a tool member is inserted, said collet being formed with longitudinal slots adapting said collet to grip said tool for operative engagement within said handpiece assembly, said bore being defined with a predetermined depth terminating interioraly of said assembly at a tool abutment surface located to be engaged by the inner end of a tool inserted into said bore, and a removable spacer member inserted into said bore to provide a substitute tool abutment surface thereby to adapt said handpiece assembly to receive a tool having a length which does not reach to said tool abutment surface when said tool is in operative engagement within said bore, said removable spacer member including a handle portion located to extend outwardly of said bore and to within one of said collet slots when said spacer member is in place within said bore.

2. An assembly according to claim 1 wherein said handle portion is formed with a bent end which extends outwardly of said collet and which is shaped in the form of a hook.

3. An assembly according to claim 2 further comprising a hollow shaft surrounding said collet, said hollow shaft including a radial front groove, said hook-shaped end of said handle portion being engaged in said radial front groove of said hollow shaft.

4. An assembly according to claim 3 including an adjustment ring rotatably mounted upon said hollow shaft, said handle portion extending into engagement with said ring for movement therewith.

5. An assembly according to claim 4 wherein said handle portion of said removable spacer member consists of a wire piece which is connected at one end with said ring mounted on said hollow shaft and which has an opposite end which is bent radially inwardly of said collet, said radially inwardly bent end extending into said bore of said collet to form therein said substitute tool abutment surface.

6. An assembly according to claim 4 wherein said adjustment ring is adapted to be moved axially of said hollow shaft in order to enable adjustment of said collet, and wherein said ring has attached thereto a projection pin extending radially inwardly of said collet which by axial displacement of said ring may be introduced simultaneously into one of said grooves of said hollow shaft and into one of said slots of said collet.

7. An assembly according to claim 6 wherein said radially extending pin is formed with an angularly bent spring wire.

8. An assembly according to claim 1 wherein said spacer member consists essentially of a helically wound wire piece having an end which extends generally linearly in a direction axially of said collet and which operates to form said handle portion.

* * * * *